(12) United States Patent
Yamamoto

(10) Patent No.: US 8,944,998 B2
(45) Date of Patent: Feb. 3, 2015

(54) ENDOSCOPE APPARATUS

(75) Inventor: Goki Yamamoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 176 days.

(21) Appl. No.: 13/361,722

(22) Filed: Jan. 30, 2012

(65) Prior Publication Data

US 2012/0220826 A1    Aug. 30, 2012

(30) Foreign Application Priority Data

Feb. 25, 2011  (JP) ................ P2011-039538

(51) Int. Cl.
  *A61B 1/04*  (2006.01)
  *A61B 1/05*  (2006.01)

(52) U.S. Cl.
  CPC ...................................... *A61B 1/051* (2013.01)
  USPC ......................................................... 600/110

(58) Field of Classification Search
  CPC ...... H01R 4/023; H01R 9/0728; H01R 9/093; H01R 12/55; H01R 12/65; H01R 12/83; H01R 13/5841
  USPC .................. 600/101, 109, 110, 129
  See application file for complete search history.

(56) References Cited

U.S. PATENT DOCUMENTS

| 4,895,138 | A | * | 1/1990 | Yabe ............................. 600/110 |
| 4,989,586 | A | * | 2/1991 | Furukawa ..................... 600/110 |
| 4,993,405 | A | * | 2/1991 | Takamura et al. ............ 600/110 |
| 5,894,369 | A | * | 4/1999 | Akiba et al. .................. 359/820 |
| 6,095,970 | A | * | 8/2000 | Hidaka et al. ................ 600/110 |
| 6,547,721 | B1 | * | 4/2003 | Higuma et al. ............... 600/133 |

FOREIGN PATENT DOCUMENTS

| JP | S63-119733 | 5/1988 |
| JP | 2009-089924 A | 4/2009 |
| JP | 2009-089925 A | 4/2009 |

* cited by examiner

*Primary Examiner* — Anhtuan T Nguyen
*Assistant Examiner* — Alexandra Newton
(74) *Attorney, Agent, or Firm* — Birch, Stewart, Kolasch & Birch, LLP

(57) ABSTRACT

In an endoscope apparatus in which an imaging element and a circuit board to which the imaging element is connected are provided inside a distal end of an insertion part, disconnection between the circuit board and a signal wiring line is prevented. In an endoscope apparatus including an insertion part to be inserted into the body, an imaging element, a circuit board electrically connected to the imaging element and arranged parallel to the longitudinal direction of the insertion part, and a signal wiring line electrically connected to the circuit board and extending in the longitudinal direction are provided within the insertion part, and a connecting portion between the circuit board and the signal wiring line is provided with a easing member that eases a force applied to the connecting portion.

17 Claims, 8 Drawing Sheets

ENDOSCOPE APPARATUS

BACKGROUND OF THE INVENTION

1. Field of the Invention

The present invention relates to an endoscope apparatus including an insertion part to be inserted into the body, and particularly, to a wiring connection structure inside the distal end of an insertion part.

2. Description of the Related Art

In the related art, an endoscope system that observes a tissue within a body cavity is widely known, and an electronic endoscope system that images a part to be observed in the body cavity using an imaging element to obtain a normal image, and displays the normal image on a monitoring screen has been widely put into practical use.

The above-described endoscope system includes an insertion part to be inserted into the body. A curvable part is provided in the vicinity of a distal end of the insertion part, and the curvable part is curved in any of the vertical and horizontal directions by rotational manipulation of a manipulating knob provided at a manipulating part at the grip of an endoscope body. Thereby, the insertability to the inside of the body of a patient can be made smooth, the distal end of the insertion part can be turned in a desired direction within the body cavity, and an image of a desired part to be observed can be captured.

A multi-conductor cable that bundles signal wiring lines connected to a light guide for guiding illumination light and an imaging element that captures an observation image is loosely inserted inside the insertion part, and for example, a CCD (Charge Coupled Device) serving as the imaging element is provided in the form of a bare chip on which packaging is not performed, inside the distal end of the insertion part. An electrode on the chip is connected to a wiring pattern formed on a circuit board, and individual signal lines in the multi-conductor cable provided to extend within the insertion part are connected to the wiring pattern of the circuit board by soldering or the like.

Here, the curvable part of the insertion part is inserted into the body as described above and is curved in various shapes. At this time, as a bending force or pulling force is applied to the multi-conductor cable provided to extend within the insertion part, there is a concern that a force may be applied to a portion connected to the wiring pattern of the circuit board, and a signal wiring line may separate from the wiring pattern of the circuit board.

Therefore, for example, JP2009-89924A suggests that a combed elastic member is provided in the vicinity of a portion of the signal wiring line connected with the circuit board so as to be entangled in a signal wiring line, thereby allowing expansion and contraction against the pulling of the insertion part in the longitudinal direction. Additionally, JP2009-89925A suggests providing an elasticity imparting unit that imparts elasticity to a multi-conductor cable, within a manipulating part of an endoscope body.

SUMMARY OF THE INVENTION

However, as described above, the distal end part of the insertion part is turned in various directions as the curvable part deforms. The inventions described in JP2009-89924A or JP2009-89925A can absorb a certain degree of a pulling force in the longitudinal direction of the insertion part, but cannot absorb the torque applied to a connecting portion between the signal wiring line and the circuit board. Thus, a concern of disconnection remains.

The invention has been made in view of the above-mentioned problems and an object thereof is to provide an endoscope apparatus that can absorb torque as well as a pulling force applied to a connecting portion between a circuit board and a signal wiring line, and can prevent disconnection between the circuit board and the signal wiring line, in the endoscope apparatus in which an imaging element and the circuit board to which the imaging element is connected are provided inside a distal end of an insertion part.

An endoscope apparatus of the present invention is an endoscope apparatus including an insertion part to be inserted into the body, an imaging element, a circuit board electrically connected to the imaging element and arranged parallel to the longitudinal direction of the insertion part, and a signal wiring line electrically connected to the circuit board and extending in the longitudinal direction being provided within the insertion part. A connecting portion between the circuit board and the signal wiring line is provided with a easing member that eases a force applied to the connecting portion.

Additionally, in the endoscope apparatus of the above invention, the easing member may include a pad member that comes into contact with a wiring pattern formed on the circuit board and has the signal wiring connected thereto, and a supporting member that swingably supports the pad member.

Additionally, the supporting member may regulate the position of the pad member.

Additionally, the supporting member may regulate the amount of movement of the pad member.

Additionally, the pad member may include a contact part that comes into contact with the wiring pattern that is formed in a spherical shape.

Additionally, the pad member may have the spherical contact part, a connecting plate part having the signal wiring line connected thereto, and a pillar part that connects the contact part and the connecting plate part to each other, and the supporting member may have a through hole into which the pillar part penetrates.

Additionally, the connecting plate part may be tilted using the pillar part as an axis.

Additionally, the through hole may be formed in a tapered shape so that the opening on the side of the pad member is larger than the opening on the side of the circuit board.

Additionally, the pillar part may be formed in a tapered shape thin toward the contact part.

Additionally, the pillar part and the connecting plate part may be formed so that the connecting plate part touches on the supporting member before the tapered portion of the pillar part comes into contact with an inner wall of the through hole when the pillar part is inclined from a direction perpendicular to the circuit board.

Additionally, the pad member may have a contact part that comes into contact with the wiring pattern that is formed in a spherical shape, and a spherical hole that the contact part swingably engages is formed in a portion of the wiring pattern as a supporting member.

According to the endoscope apparatus of the present invention, the endoscope apparatus may include an insertion part to be inserted into the body. An imaging element, a circuit board electrically connected to the imaging element and arranged parallel to the longitudinal direction of the insertion part, and a signal wiring line electrically connected to the circuit board and extending in the longitudinal direction are provided within the insertion part. A connecting portion between the circuit board and the signal wiring line may be provided with a easing member that eases a force applied to the connecting portion. Thus, torque as well as a pulling force applied to a connecting portion between the circuit board and the signal wiring line can be absorbed by the easing member, and disconnection between the circuit board and the signal wiring line can be prevented.

DESCRIPTION OF THE PREFERRED EMBODIMENTS

Figure 1:
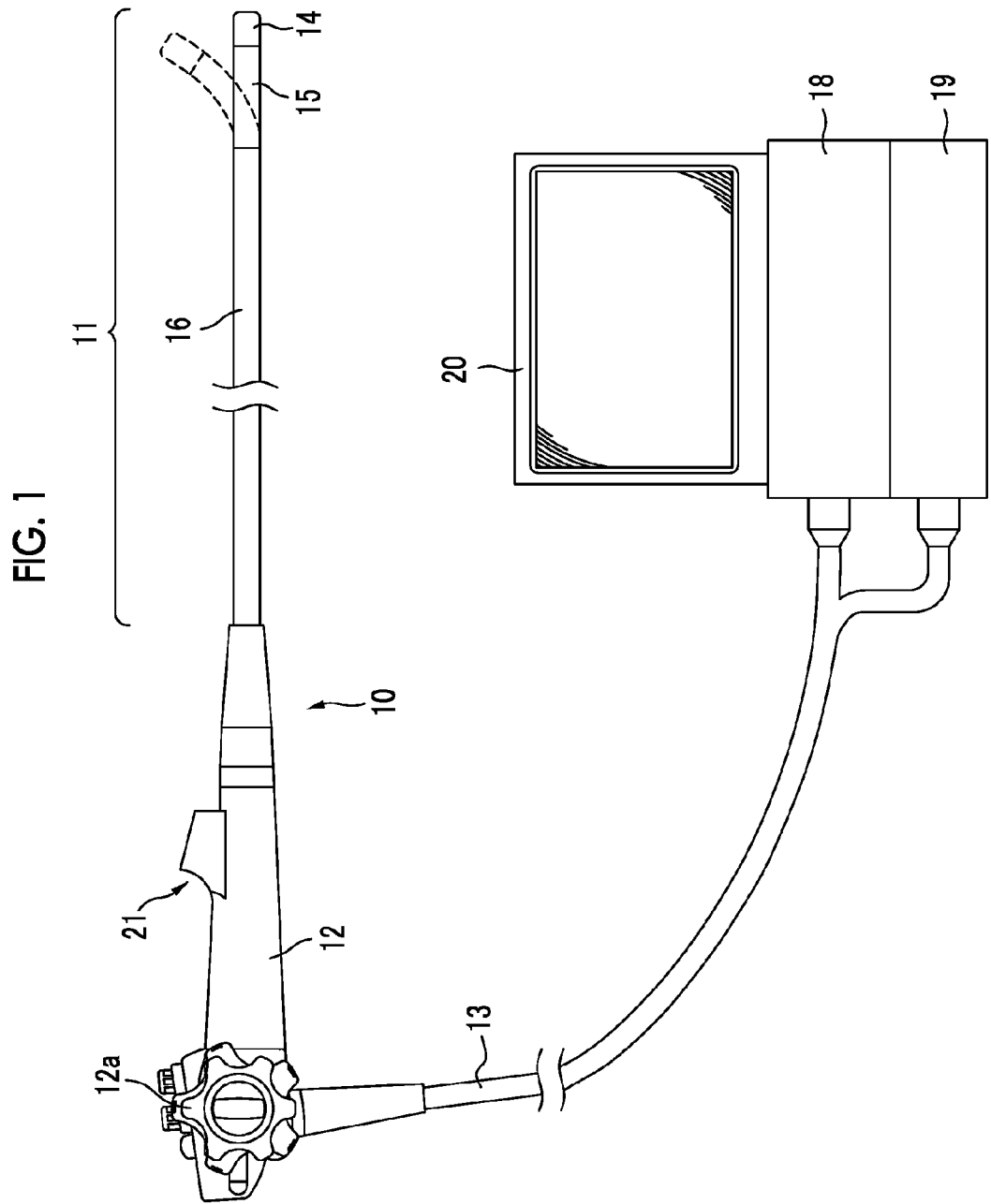
FIG. 1 is an outline view showing the schematic configuration of an endoscope system using one embodiment of an endoscope apparatus of the present invention.

An endoscope system using one embodiment of an endoscope apparatus of the present invention will be described below in detail with reference to the drawings. Although the present embodiment has the special feature of a wiring connection structure inside the distal end of an insertion part to be inserted into the body, the configuration of the overall system will first be described. FIG. 1 is an outline view showing the schematic configuration of the endoscope system of the present embodiment.

As shown in FIG. 1, the endoscope system of the present embodiment includes an endoscope body 10, a universal cable 13 having one end connected to the endoscope body 10, a processor device 18 and a light source device 19 to which the other end of the universal cable 13 is connected, and a monitor 20 that displays an image on the basis of an image signal output from the processor device 18.

The endoscope body 10 includes an insertion part 11 to be inserted into the body, and a manipulating part 12 that receives predetermined manipulation of a manipulator. The insertion part 11 is formed in a tubular shape, and specifically, includes a distal end hard part 14, a curvable part 15, and a flexible tube part 16 sequentially from the distal end as shown in FIG. 1.

The distal end hard part 14 is formed from a hard metallic material or the like, and the flexible tube part 16 is a portion that connects the manipulating part 12 and the curvable part 15 in a long shape with a fine diameter, and has flexibility. The curvable part 15 operates to be curved as an angle wire inserted into the insertion part 11 is pushed and pulled interlocking with the manipulation of an angle knob 12a provided at the manipulating part 12. Thereby, the distal end hard part 14 is turned in a desired direction within the body, and a desired part to be observed is imaged by an imaging element (to be described below) provided within the distal end hard part 14. Additionally, the manipulating part 12 is provided with a forceps port 21 through which a treatment tool is inserted, and the forceps port 21 is connected to a forceps tube 26 (to be described below) that is arranged within the insertion part 11.

Figure 2:
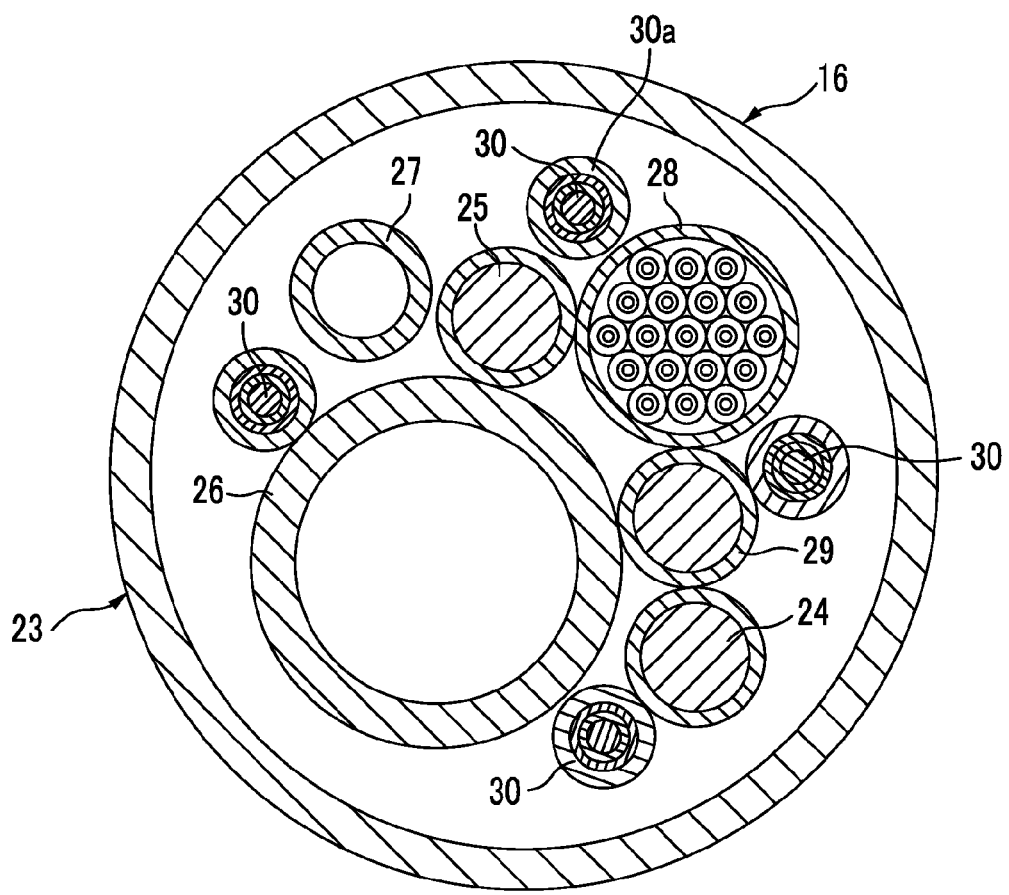
FIG. 2 is a cross-sectional view showing the inside of a flexible tube part of an insertion part.

As shown in FIG. 2, the flexible tube part 16 is configured such that a plurality of contents, such as light guides 24 and 25 for guiding illumination light to an illumination lens of the distal end hard part 14, a forceps tube 26, an air supply and water supply tube 27, a multi-conductor cable 28, and a jet-spray tube 29 are loosely inserted into a flexible tube 23. The multi-conductor cable 28 is provided by putting together, mainly, control signal wiring line for sending a control signal for driving an imaging element from the processor device 18, an image signal wiring line for sending an image signal imaged by an imaging element to the processor device 18, and the plurality of signal wiring lines is covered with a protective coating. In addition, reference numeral 30 represents an angle wire for manipulating the curvable part 15, and is inserted through an adhesion coil pipe 30a.

Figure 3:
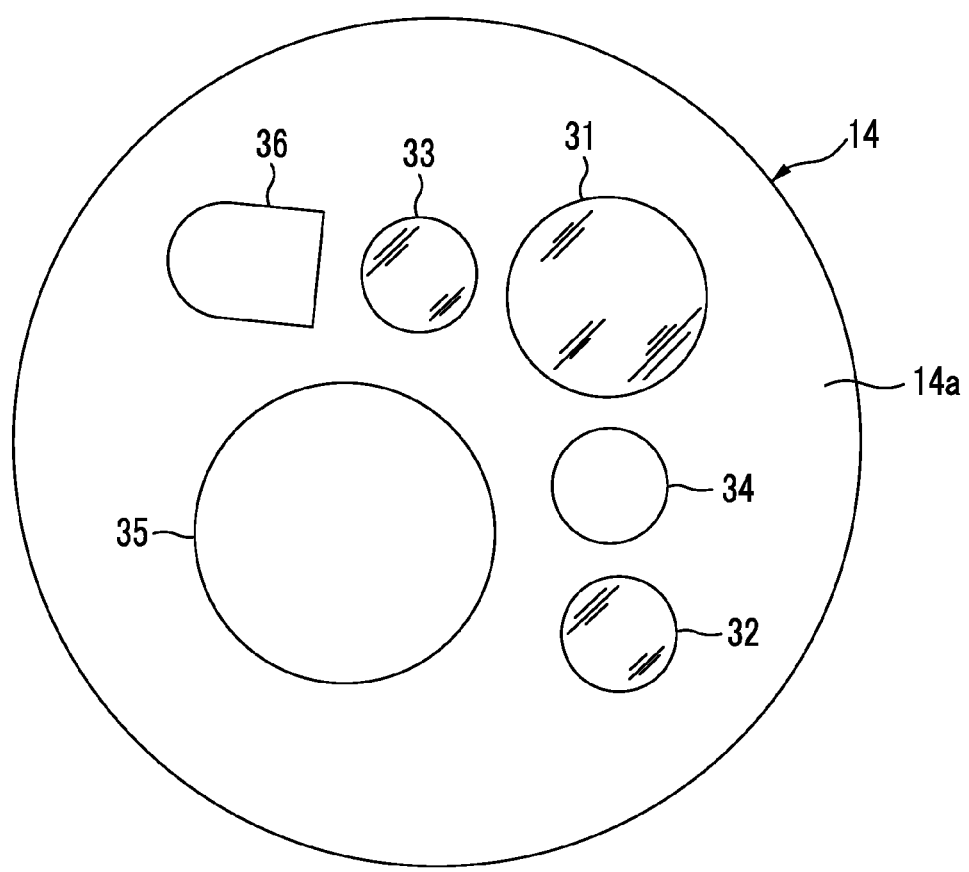
FIG. 3 is a view showing the configuration of a distal end of the insertion part.

As shown in FIG. 3, a distal end face 14a of the distal end hard part 14 is provided with an observation window 31, illumination windows 32 and 33, a jet-spray port 34, a forceps outlet 35, an air supply and water supply nozzle 36, and the like. A portion of an objective optical system for importing image light of a part to be observed within the body is arranged at the observation window 31. The illumination windows 32 and 33 have a portion of the illumination lens assembled thereinto, and allows the illumination light emitted from the light source device 19 and guided by the light guides 24 and 25 to be irradiated to a part to be observed within the body therethrough. The forceps outlet 35 communicates with the forceps port 21 provided in the manipulating part 12 via the forceps tube 26. The air supply and water supply nozzle 36 manipulates air supply and the water supply buttons provided at the manipulating part 12, thereby jetting washing water or air for removing dirt on the observation window 31. The jet-spray port 34 allows a fluid, for example, air, carbon dioxide gas, or the like, which is supplied from an air supply device, to be jetted toward a part to be observed therethrough.

Figure 4:
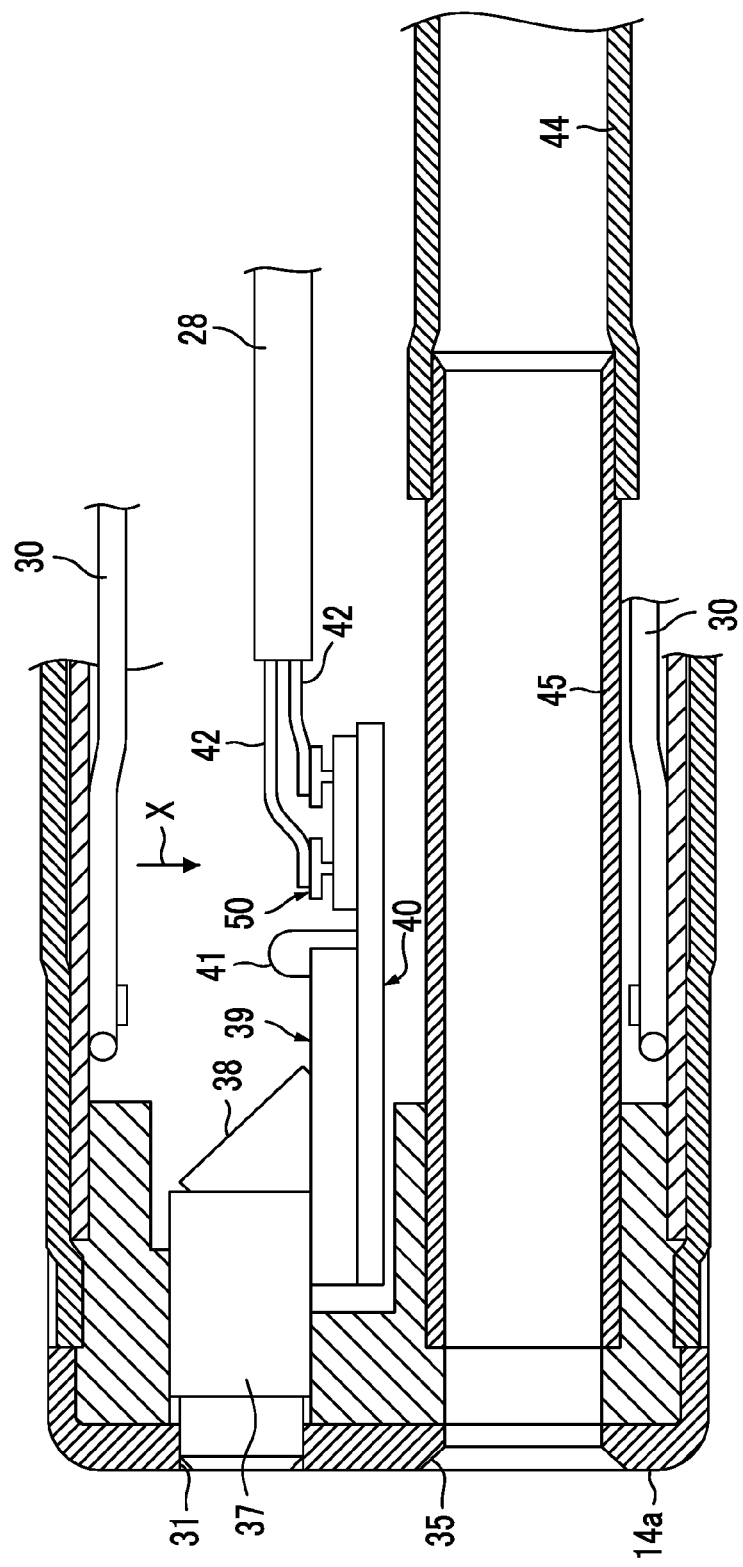
FIG. 4 is a cross-sectional view showing the inside of the distal end of the insertion part.

As shown in FIG. 4, an objective optical system 37 is arranged at a position that faces the observation window 31. The illumination light emitted from the illumination windows 32 and 33 is reflected by a part to be observed, and enters the observation window 31. An image of a part to be observed that has entered from the observation window 31 enters a prism 38 through the objective optical system 37, and is refracted inside a prism 38 and thereby formed on an imaging surface of the imaging element 39. As the imaging element 39, for example, a CCD sensor, a CMOS (Complementary Metal Oxide Semiconductor) sensor, or the like is used. However, in the present embodiment, the imaging element has a form of a bare chip in which packaging is not performed, and an electrode on the chip is connected to a wiring pattern on a circuit board 40 via a connection line 41 by methods, such as wire bonding, TAB (Tape Automated bonding), and a flip chip.

The circuit board 40 is disposed parallel to the longitudinal direction of the insertion part 11, and is fixed inside the distal end hard part 14. A wiring pattern for transferring a control signal input to the imaging element 39 or an image signal output from the imaging element 39 to a control signal wiring line or an image signal wiring line (these are collectedly referred to as signal wiring lines) of the multi-conductor cable 28 is formed on the circuit board 40.

A plurality of signal wiring lines 42 is exposed from the end of the multi-conductor cable 28 disposed parallel to the longitudinal direction of the insertion part 11, and the plurality of signal wiring lines 42 is electrically connected to the wiring pattern of the circuit board 40 via a easing member 50. The detailed configuration of the easing member 50 will be described below in detail.

Although the signal wiring lines 42 are insulated wires covered with an insulator around a conductor, a conductor obtained by removing an insulator from each signal wiring line 42 is connected to the easing member 50.

A flexible tube 44 made of synthetic resin is arranged inside the curvable part 15. The forceps tube 26 is connected to one end of the flexible tube 44, and a rigid pipe 45 arranged inside the distal end hard part 14 is connected to the other end. The rigid pipe 45 is fixed inside the distal end hard part 14, and has a distal end connected to the forceps outlet 35.

Here, if the flexible tube part 16 is bent or the curvable part 15 operates to be curved, the base of the multi-conductor cable 28 is fixed inside the manipulating part 12. Thus, the multi-conductor cable 28 can be pulled toward the manipulating part 12, and accordingly, the signal wiring lines 42 is also pulled with respect to the circuit board 40. As the multi-conductor cable is pulled toward the manipulating part 12 beyond a predetermined length, disconnection of the signal wiring lines 42, peeling-off a solder of the distal end of the signal wiring lines 42, or the like occurs.

Therefore, in the endoscope system of the present embodiment, a easing member 50 for reducing, that is, easing a forced applied to a connecting portion of the signal wiring lines 42 by such pulling of the signal wiring lines 42 is provided.

Figure 5:
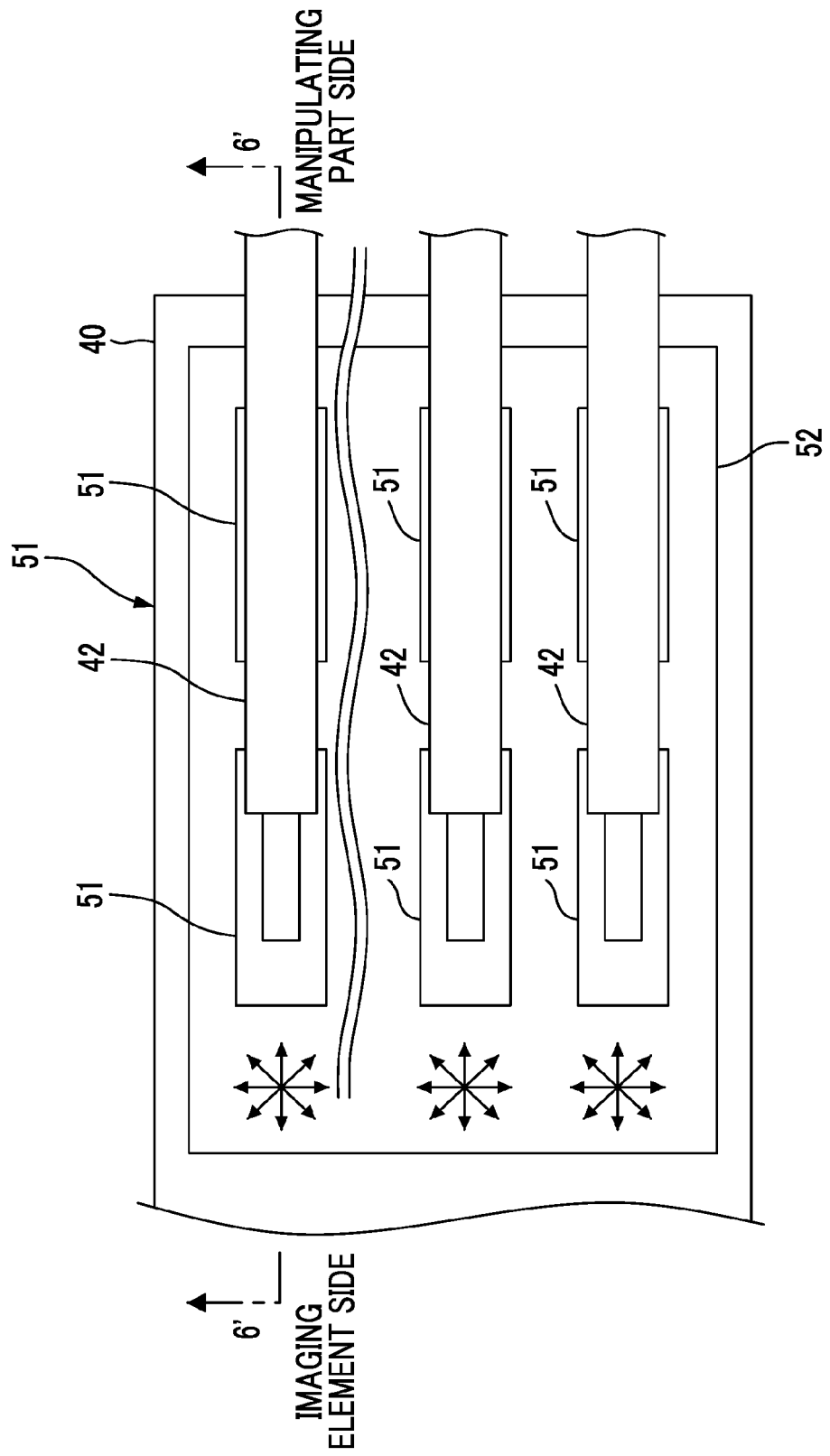
FIG. 5 is a view when a easing member shown in FIG. 4 is seen from the direction of an arrow X.
Figure 6:
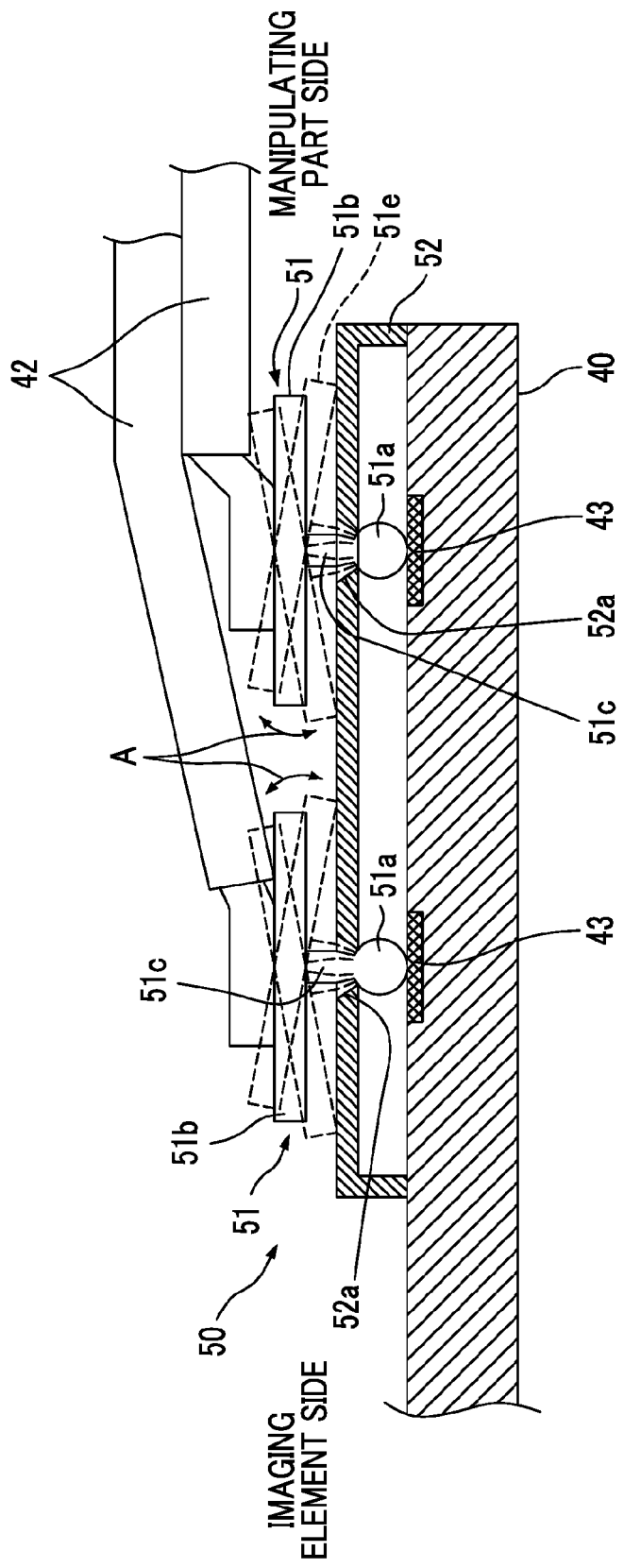
FIG. 6 is a cross-sectional view taken along the line 6-6', of the easing member shown in FIG. 5.
Figure 7:
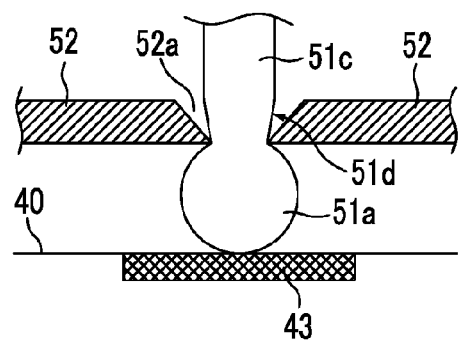
FIG. 7 is a partially enlarged view of pad members and a supporting member shown in FIG. 6.

Here, the detailed configuration of the easing member 50 will be described, referring to FIG. 7 from FIG. 5. FIG. 5 is a view when the signal wiring lines 42 and the easing member 50 shown in FIG. 4 is seen from the direction of an arrow X, FIG. 6 is a cross-sectional view taken along the line 6-6' of FIG. 5, and FIG. 7 is a partially enlarged view of FIG. 6. In addition, in FIG. 5, the two upper and lower signal wiring lines 42 shown in FIG. 4 are shown in an overlapping manner, and the lower signal wiring line is arranged immediately below the upper signal wiring line. Thus, the lower signal wiring line is hidden and is not visible.

As shown in FIGS. 5 and 6, the easing member 50 includes pad members 51 that comes into contact with the wiring pattern 43 formed on the circuit board 40 and to which the signal wiring lines 42 is connected with solder or the like, and a supporting member 52 that swingably supports the pad members 51.

The pad members 51 are provided at the individual signal wiring lines 42, respectively. Specifically, as shown in FIG. 6, each pad member is constituted by a contact part 51a that comes into direct contact with the wiring pattern 43 and is formed in a spherical shape, a rectangular connecting plate part 51b to which the signal wiring line 42 is directly connected with solder or the like, and a cylindrical pillar part 51c that connects the contact part 51a and a connecting plate part 51b. All of these are formed from conductors, such as metal.

The supporting member 52 is formed in a box shape having a predetermined space, using an insulating material, and as shown in FIG. 6, is provided in a state where a box shape is turned down on the circuit board 40. The supporting member 52 is formed with a through hole 52a into which the pillar part 51c of the pad member 51 penetrates.

FIG. 7 is an enlarged view of the vicinity of the through hole 52a of the supporting member 52. The supporting member 52 is formed at such a height that the contact part 51a of the pad member 51 comes into direct contact with the wiring pattern 43 of the circuit board 40, and does not float. As shown in FIG. 7, the through hole 52a of the supporting member 52 is formed in a tapered shape so that the diameter of an opening on the side of the connecting plate part 51b of the pad member 51 become larger than the diameter of an opening on the side of the circuit board 40. The opening of the through hole 52a on the side of the circuit board 40 is formed with such a diameter that the contact part 51a of the pad member 51 does not deviate from the wiring pattern 43 and the pillar part 51c of the pad member 51 is rotatable about a central axis. This regulates the position of the pad member 51. The diameter of the opening of the through hole 52a on the side of the connecting plate part 51b is formed with such a diameter that the pillar part 51c of the pad member 51 can be tilted.

The pillar part 51c of the pad member 51 is formed in a tapered shape thin toward the contact part 51a. The amount of taper of this tapered portion is such that an outer peripheral surface 51d of the tapered portion does not come into contact with the inner wall of the through hole 52a when the pillar part 51c of the pad member 51 is tilted. That is, when the pad member 51 is tilted as shown by a dotted line in FIG. 6, the amounts of taper of the through hole 52a and the pillar part 51c are set so that an end 51e of the connecting plate part 51b of the pad member 51 comes into contact with the supporting member 52 before the outer peripheral surface of the tapered portion comes into contact with the inner peripheral surface of the through hole 52a. Such a configuration regulates the amount of movement of the pad member 51, whereby it is possible to avoid a force being applied to the connecting portion between the connecting plate part 51b and the pillar part 51c of the pad member 51, and durability can be improved.

By configuring the easing member 50 as described above, the pad member 51 to which the signal wiring line 42 is connected can rotate in all the directions about a contact point between the contact part 51a and the wiring pattern 43 of the circuit board 40, and the connecting plate part 51b of the pad member 51 can swing in the direction of an arrow A shown in FIG. 6. Thus, torque can also be eased in addition to a pushing force or a pulling force to the signal wiring line 42 in a direction shown by the arrow in FIG. 5.

In addition, it is desirable that the face of the signal wiring line 42 connected with the connecting plate part 51b of the pad member 51 and the surface of the spherical contact part 51a expose a conductor, and other faces of the pad member 51 are covered with an insulating coating or the like.

Figure 8:
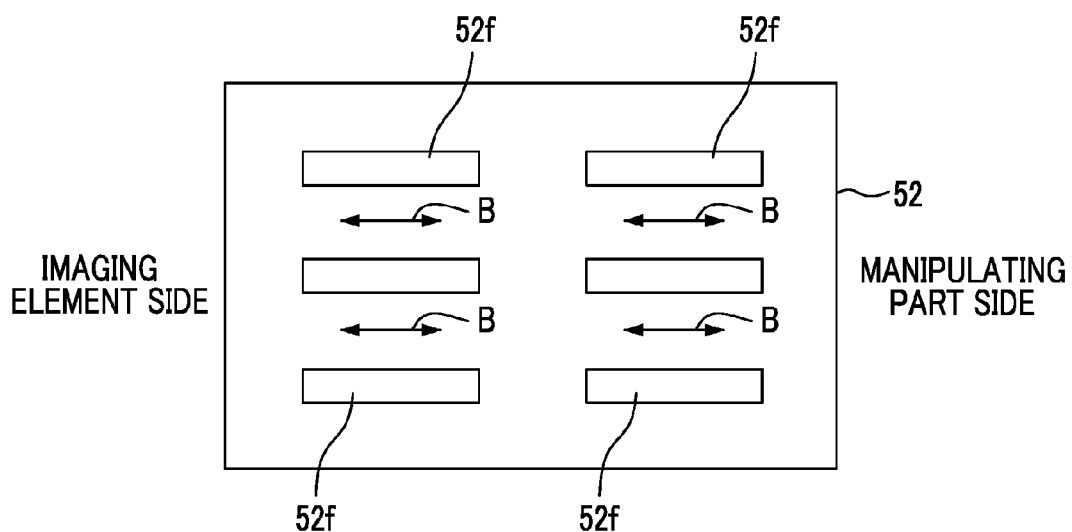
FIG. 8 is a view showing another embodiment of the supporting member in the easing member of the present invention.

In the above embodiment, the circular through hole 52a is provided in the supporting member 52. However, the present invention is not limited thereto. As shown in FIG. 8, the supporting member 52 is provided with a rectangular through hole 52f that extends in the longitudinal direction of the insertion part 11. Thereby, the pad member 51 can swing by a longer distance in the direction of an arrow B, and the permissible amount of the pushing force or the puling force in the longitudinal direction of the insertion part 11 can be increased. It is noted that it is necessary to increase the length of the rectangular through hole 52f in the longitudinal direction so that the pad member 51 does not deviate from the wiring pattern 43 of the circuit board 40.

Figure 9:
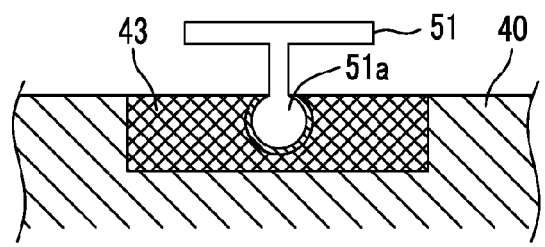
FIG. 9 is a view showing still another embodiment of the easing member of the present invention.

Additionally, in the above embodiment, the pad member 51 is supported by the supporting member 52 made of an insulating member. However, the present invention is not limited thereto. For example, as shown in FIG. 9, the pad member 51 may be supported by the wiring pattern 43 by forming a spherical hole in the wiring pattern 43 provided on the circuit board 40 and swingably engaging this hole with the contact part 51a. That is, a portion of the wiring pattern 43 may be formed as a supporting member for the pad member 51. In addition, in a case where the configuration as shown in FIG. 9 is adopted, for example, if the contact part 51a of the pad member 51 is formed from a conductive elastic body, the contact part can be pushed into the spherical hole of the wiring pattern 43.

Figure 10:
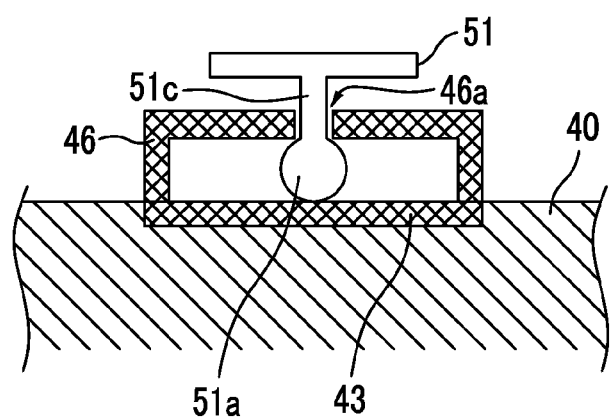
FIG. 10 is a view showing still further embodiment of the easing member of the present invention.

Otherwise, as shown in FIG. 10, a conductor supporting member 46, which is formed from conductors, such as metal, and formed in a box shape, may be formed on the wiring pattern 43, and the pad member 51 may be supported by the conductor supporting member 46. Even in this case, it is desirable that the height of the conductor supporting member 46 is set to such a height that the contact part 51a of the pad member 51 does not separate from the wiring pattern 43, and the through hole 46a into which the pillar part 51c of the pad member 51 penetrates is also formed in a tapered shape similarly to the above embodiment.

Figure 11:
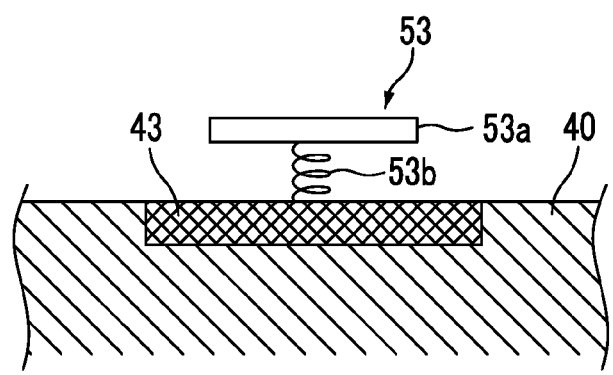
FIG. 11 is a view showing still further embodiment of the easing member of the present invention.

Additionally, the pad member to which the signal wiring line is connected is not limited to the shape as in the above embodiment. For example, as shown in FIG. 11, a plate shaped connecting plate part 53a to which the signal wiring line 42 is directly connected may be provided as a pad member, and a connecting spring part 53b that connects the connecting plate part 53a and the wiring pattern 43 of the circuit board 40 and is made of a conductive spring member may be provided as a supporting member.

Additionally, flexibility may be provided to the connecting portion by connecting the signal wiring line 42 and the wiring pattern 43 of the circuit board 40 with conductive paste in which a conductor, such as silver, is mixed with a resin material, such as silicon.

What is claimed is:

1. An endoscope apparatus comprising:
   an insertion part to be inserted into the body,
   an imaging element, a circuit board electrically connected to the imaging element and arranged parallel to a longitudinal direction of the insertion part, and a signal wiring line electrically connected to the circuit board and extending in the longitudinal direction being provided within the insertion part,
   wherein a connecting portion between the circuit board and the signal wiring line is provided with a easing member that eases a force applied to the connecting portion,
   wherein the easing member includes a pad member that comes into contact with a wiring pattern formed on the circuit board and has the signal wiring connected thereto, and a supporting member that swingably supports the pad member.

2. The endoscope apparatus according to claim 1, wherein the supporting member regulates the position of the pad member.

3. The endoscope apparatus according to claim 1, wherein the supporting member regulates the amount of movement of the pad member.

4. The endoscope apparatus according to claim 2, wherein the supporting member regulates the amount of movement of the pad member.

5. The endoscope apparatus according to claim 1, wherein the pad member includes a spherical contact part that comes into contact with the wiring pattern.

6. The endoscope apparatus according to claim 2, wherein the pad member includes a spherical contact part that comes into contact with the wiring pattern.

7. The endoscope apparatus according to claim 5,
   wherein the pad member has the spherical contact part, a connecting plate part having the signal wiring line connected thereto, and a pillar part that connects the contact part and the connecting plate part to each other, and
   wherein the supporting member has a through hole into which the pillar part penetrates.

8. The endoscope apparatus according to claim 6,
   wherein the pad member has the spherical contact part, a connecting plate part having the signal wiring line connected thereto, and a pillar part that connects the contact part and the connecting plate part to each other, and
   wherein the supporting member has a through hole into which the pillar part penetrates.

9. The endoscope apparatus according to claim 7, wherein the connecting plate part is tilted using the pillar part as an axis.

10. The endoscope apparatus according to claim 8, wherein the connecting plate part is tilted using the pillar part as an axis.

11. The endoscope apparatus according to claim 9, wherein an opening of the through hole on the side of the pad member is larger than an opening of the through hole on the side of the circuit board.

12. The endoscope apparatus according to claim 10, wherein an opening of the through hole on the side of the pad member is larger than an opening of the through hole on the side of the circuit board.

13. The endoscope apparatus according to claim 9, wherein the pillar part has a portion formed thin toward the contact part.

14. The endoscope apparatus according to claim 10, wherein the pillar part has a portion formed thin toward the contact part.

15. The endoscope apparatus according to claim 13, wherein the pillar part and the connecting plate part are formed so that the connecting plate part touches on the supporting member before the pillar part comes into contact with an inner wall of the through hole when the pillar part is inclined from a direction perpendicular to the circuit board.

16. The endoscope apparatus according to claim 14, wherein the pillar part and the connecting plate part are formed so that the connecting plate part touches on the supporting member before the pillar part comes into contact with an inner wall of the through hole when the pillar part is inclined from a direction perpendicular to the circuit board.

17. The endoscope apparatus according to claim 1,
   wherein the pad member has a spherical contact part that comes into contact with the wiring pattern, and
   wherein a portion of the wiring pattern is formed with a spherical hole that the contact part swingably engages.

* * * * *